United States Patent [19]

Gardner et al.

[11] Patent Number: 4,850,691
[45] Date of Patent: Jul. 25, 1989

[54] METHOD AND APPARATUS FOR DETERMINING PUPILLARY RESPONSE PARAMETERS

[75] Inventors: Chester S. Gardner, Champaign, Ill.; Kirk S. Schroeder, Ann Arbor, Mich.; Richard Kast, Barrow, Ak.

[73] Assignee: University of Illinois, Urbana, Ill.

[21] Appl. No.: 27,466

[22] Filed: Mar. 18, 1987

[51] Int. Cl.[4] .............................................. A61B 3/10
[52] U.S. Cl. .................................... 351/221; 351/210
[58] Field of Search ............... 351/221, 205, 208, 206, 351/212, 209, 210, 213

[56] References Cited

U.S. PATENT DOCUMENTS

| Re. 28,415 | 5/1975 | Robinson et al. | 351/6 |
|---|---|---|---|
| 3,450,466 | 6/1969 | Streisinger | 351/7 |
| 3,473,868 | 10/1969 | Young et al. | 351/6 |
| 3,984,156 | 10/1976 | Jernigan | 351/6 |
| 4,149,787 | 4/1979 | Kobayashi et al. | 354/62 |
| 4,169,663 | 10/1979 | Murr | 351/7 |
| 4,387,974 | 6/1983 | Marshall et al. | 351/210 |
| 4,397,531 | 8/1983 | Lees | 351/210 |

OTHER PUBLICATIONS

Bellarminov, Pflugers Arch. Ges. Phusiol., 37. 7, 1885.
Lowenstein et al., Pupillographic Studies, Arch. of Ophthal., 27, 969-993, 1942.
Lowenstein and Lowenfeld, Electronic Pupillography, AMA Arch. of Ophthal., 59, 352-363, 1958.
Ishikawa et al., A New Vedeopupillography, Opthalmalogica, 160, 248-259, 1970.
Matsunaga, A New Binocular Electronic Scanning Pupillometer, Physiologia, 16, 115-120, 1973.
Watanabe, A Solid State Television Pupillometer, Vision Research, 22, 499-505, 1952.
Jones et al. A New Solid State Dynamic Pupillometer Using A Self-Scanning Photodiode Array, Journal of Physics E: Scientific Instruments, 16, 1169, 1983.
Stark, Stability, Oscillations, And Noise In The Human Pupil Servomechanism, Proceedings of the IRE, Nov. 1959.
Zuber et al., A Simple Inexpensive Electronic Pupillometer, Vision Research, 5, 695-696, 1965.
Cassady, Pupillary Activity Measured by Reflected Infra-Red Light, Physiology and Behavior, 28, 851-854, 1982.
Alexandridis et al., The Latent Period of the Pupil Light Reflex in Legions of the Optic Nerve, Ophthalmalogica, Basel, 182, 211-217, 1981.
Lowenfeld et al., Influence of Pupil Size on Dynamics of Pupillary Movements, Amer. Jour. of Ophthal., 71, 347-362, 1971.
C. Ellis, Journal of Neurology, Neurosurgery, and Psychiatry, 42, 1008-1017, 1979.
Kase et al., Pupillary Light Reflex in Amblyopia, Invest. Ophthal. and Vis. Sci, 467-471, 1981.
Braakman et al., Systematic Selection of Prognostic Features In Patients with Severe Head Injury, Neurosurgery, 6, 362-369, 1980.
American Medical News, Mar. 15, 1985, p. 55.
AFP, vol. 31, No. 3, p. 192.
Lowenfeld et al., Iris Mechanics, Influence of Pupil Size on Dynamics of Pupillary Movements, American Journal of Ophthalmology, 1971.

(List continued on next page.)

Primary Examiner—Rodney B. Bovernick
Assistant Examiner—P. M. Dzierzynski
Attorney, Agent, or Firm—Martin M. Novack

[57] ABSTRACT

Method and apparatus are disclosed for determining pupillary response parameters, such as latency, time of acceleration of constriction, and speed of constriction. In a form of the disclosed method a signal is derived which is representative of measured pupil size as a function of time after a visible light stimulus. The signal is modified to remove therefrom artifacts due to eye movement. Pupillary response parameters can be obtained from the modified signal. In a preferred embodiment, the modifying of the signal includes fitting curves to different portions of the signal, correcting at least one of the fitted curves, and deriving the modified signal from the curves, as corrected.

34 Claims, 11 Drawing Sheets

OTHER PUBLICATIONS

Johnson et al., The Photomyoclonic Reflex: An Artifact in the Clinical Electroretinogram, Brit. Journal of Ophthal., 66, 1982.

Alpern et al., The Dependence of the Photopupil Response on Flash Duration Intensity, Jour. of Gen. Phys., 47, 265–278, 1963.

Davson, The Physiology of the Eye, Little Brown & Co., G. B. 1963.

Ellis, The Pupillary Light Reflex in Normal Subjects, Brit. Jour. of Ophthal., 65, 754–759, 1981.

Sliney et al., Evaluation of Optical Radiation Hazards, Appl. Opt., 12, 1–24, 1973.

Webster, Pupillary Light Reflex: Development of Teaching Models, IEEE Transactions on Bio-Medical Engineering, vol. BME-18 No. 3, May 1971.

Maletinsky, Modelling and Identification of the Pupillary Light Reflex System, IEEE CH1486-0/79/00-00-0526, pp. 526–527, 1979.

Newsome et al., Iris Mechanics II. Influence of Pupil Size on Details of Iris Structure, American Journal of Ophthalmology, vol. 71, No. 2, Feb. 1971.

Lowenstein et al., Influence of Retinal Adaptation Upon the Pupillary Reflex to Light in Normal Man, Pupillary Reflex to Light, pp. 644–653.

Safran et al., Pupil Cycle Induction Test: A Way of Evaluating the Pupillary Light Reflex, Pupil Cycle Induction Text, Opthalmologica, Basel 183: 205–213 1981.

Lowenstein, Pupillary Methods and Diagnostic System Opthalmology Illustrated, A.M.A. Archives of Opthalmology, pp. 565–571, Nov. 21, 1955.

Gundersen, A New Photostimulator and Videopupillograph for Quantitative Neuroophthalmological Studies, Opthalmologica, Basel 172: 62–68 1976.

Applied Science Laboratories, "Update 84" Eye View Monitor Literature (4 sheets).

Applied Science Laboratories, Helmet Mounted Eye View Monitor Literature (2 sheets).

Applied Science Laboratories, ASL-210 Literature (1 sheet).

Applied Science Laboratories, Eye Track Literature (32 sheets).

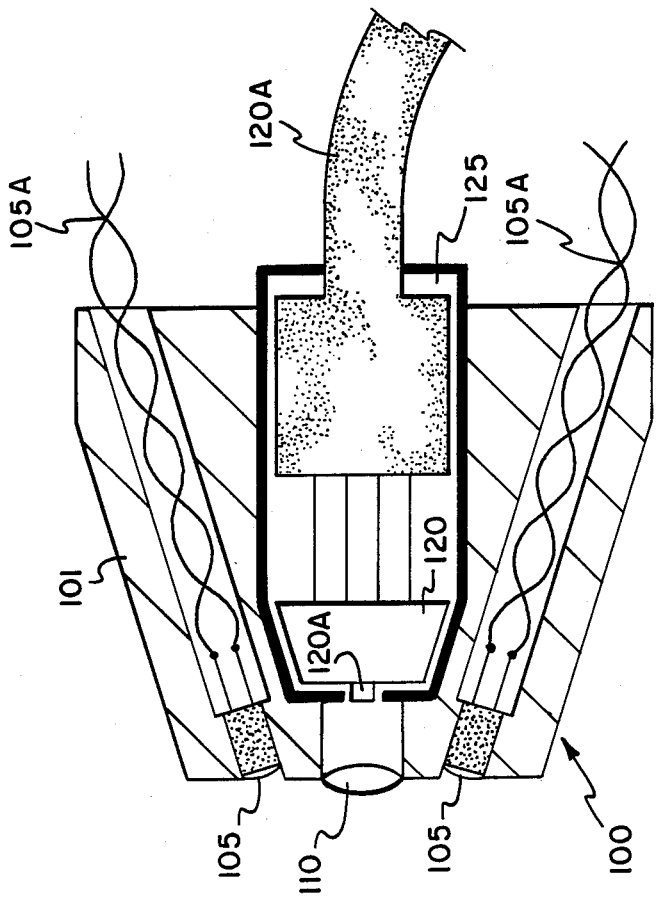
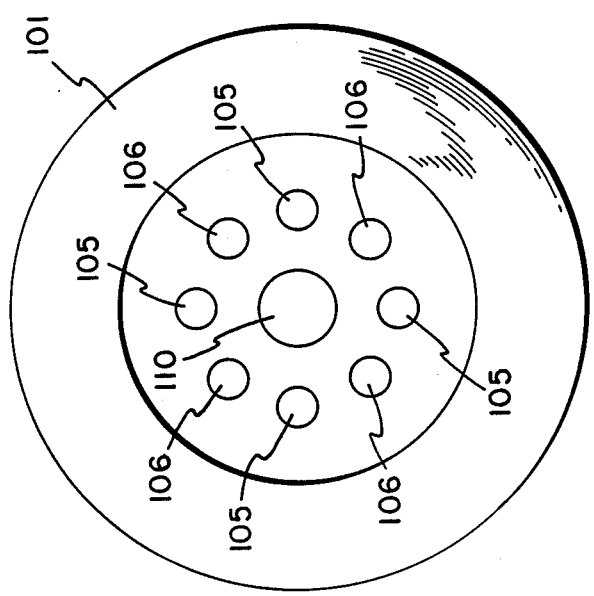
Fig. 3A
Fig. 3B

METHOD AND APPARATUS FOR DETERMINING PUPILLARY RESPONSE PARAMETERS

BACKGROUND OF THE INVENTION

This invention relates to apparatus and method for measuring pupillary response parameters, particularly for diagnostic purposes.

The study of pupillary movement in the eyes of humans and animals has evolved considerably over the past hundred years. Physicians and scientists alike have utilized the dynamics of the pupil as a unique and sensitive indicator for a wide range of neurological and physiological process. An early attempt at a recording of this movement was the work of Bellarminov (Pflugers Arch. ges. Physiol., 37, 7, 1885). By placing a glass rod in front of the eye which was illuminated from the side, a dispersed image of the pupil was formed. This image was subsequently recorded continuously on film. Cinematographic techniques using ultraviolet radiation first and infrared radiation later were developed by Lowenstein et al. (Pupillographic Studies, Arch. of Ophthal., 25, 969–993, 1942). This method permitted simultaneous filming of both eyes, and by measuring the individual film frames, a plot of pupil diameter versus time was obtained. However, this technique had several drawbacks, including poor time resolution due to slow frame rates, the use of expensive IR film, and the large amount of manual processing time required.

Some of these difficulties were overcome by a device developed by Lowenstein and Lowenfeld (Electronic Pupillography, AMA Arch. of Ophthal., 59, 352–363, 1958). This device used a rotating drum to project successive infrared beams horizontally across the eye. Since the iris reflects IR radiation better than the pupil, each horizontal sweep across the eye would result in a reflected square pulse with a duration proportional to the distance across the pupil at that point. Electronic circuitry converted the maximum pulse duration (corresponding to the diameter of the pupil) into a voltage which was then recorded. By utilizing this technique, the instrument was able to measure changes in pupil diameter as small as 0.025 mm as well as provide a plot of pupil diameter versus time automatically. However, the device was expensive and cumbersome for use in a clinical applications and was limited in time resolution due to the mechanical scanning involved.

Ishikawa et al. (A New Videopupillography, Ophthalmalogica, 160, 248–259, 1970), developed an instrument to measure the pupil area using a closed-circuit IR television system. Through proper calibration, the pupil area measurement was then converted to one of pupil diameter. This particular system used approximately the same type of horizontal slice imaging introduced by Lowenstein with an improved accuracy of 500 slices/frame and an enhanced time resolution of up to 100 frames/sec. One principal advantage of this approach was the ability to display the video signal on a monitor, which facilitated optical alignment of the subject with respect to the system.

A more recent innovation in TV systems of this type included the development of a single horizontal scan line pupillometer which, when properly aligned, directly detects the pupil diameter (Matsunaga, A New Binocular Electronic Scanning Pupillometer, Physiologia, 16, 115–120, 1973). The move towards single line imaging was initiated by the presence of signal artifacts due to anomalies such as drooping eyelids. Some of the problems inherent in this particular device, such as image lag and distortion, have been removed with the development of a solid-state TV pupillometer (see Watanabe, A Solid State Television Pupillometer, Vision Research, 22, 499–505, 1982).

In general, IR television pupillometers provide very good results. However, the quality of electro-optic components necessary to provide such results makes the systems rather expensive for clinical applications. Also, the fastest frame rates reported in the literature of 100 frames/sec (corresponding to a 10 ms time resolution) has still not been shown to be precise enough for an accurate clinical determination of important parameters describing pupillary movement.

Some research has been directed towards building more cost-effective pupillometers. Jones et al. (A New Solid State Dynamic Pupillometer Using A Self-Scanning Photodiode Array, Journal of Physics E: Scientific Instruments, 16, 1169, 1983) developed a dynamic IR pupillometer utilizing a 100-element linear self-scanning photodiode array to measure the diameter of the pupil. While fairly inexpensive and accurate, this device is limited in time resolution to 20 ms due to rise time constraints of the photodiode array.

A method of monitoring pupil dynamics through detection of pupil area was set forth by Stark (Stability, Oscillations, And Noise In The Human Pupil Servomechanism, Proceedings of The IRE, November 1959). Illumination of the eye with IR radiation results in a reflected signal which is proportional to the iris area. For a fixed detector field of view, the signal is therefore also proportional to the pupil area. While not yielding a direct measurement of pupil diameter, this approach can provide accurate quantitative evaluations of various dynamic pupil movements at a great reduction in complexity and cost (in comparison to the TV systems). An earlier device which monitored pupil area using an IR-sensitive solid-state sensor to detect reflected radiation from the eye was disclosed by Zuber et al. (A Simple Inexpensive Electronic Pupillometer, Vision Research, 5, 695–696, 1965). This device was used to illustrate the instability oscillations in the pupil area due to the presence of a light stimulus on the edge of the iris/pupil interface. A similar device by Cassady was used to monitor changes in the pupil area of paralyzed cats, but was never applied to human subjects (see Cassady, Pupillary Activity Measured By Reflected Infra-Red Light, Physiology And Behavior, 28, 851–854, 1982).

The patent literature also contains examples of instruments and methods for measuring pupillary and other eye characteristics.

U.S. Pat. No. 3,450,466 discloses an eye movement recorder in which a beam is scanned on the surface of an eye and reflected by the eye onto a photomultiplier. The patent states that since the scan is controlled in relationship to the iris and sclera of the eye, the reflected light spot will vary in intensity depending on its relative position on the overall eye surface. The maximum reflected light intensity, and the time of the maximum, are recorded and compared in phase and intensity against a reference, to obtain a record of eye movement.

U.S. Pat. No. 3,473,868 discloses equipment for measuring eye position and movement, and pupil area. Infrared light is reflected off the eye to obtain measurements. In one application of the patented equipment, the upper eyelid is blackened to decrease its reflectivity when it is in the field of view.

U.S. Pat. No. 3,984,156 discloses an eye movement monitoring system which is used in measuring and evaluating a subject's visual field. Determination of whether the subject has seen or missed a particular target is evaluated by logic systems which discriminate between eye movement and positions displaying characteristics indicative of whether the subject has seen or missed the target. The logic discriminates between blinks, hunting eye movements and other characteristic positions and movements which are indicative of the subject having seen the target.

Other U.S. Patents pertaining to eye measurements are U.S. Pat. Nos. 4,149,787, 4,169,663, 4,387,974, 4,397,531 and Re 28,415.

The relationship of pupillary light response ("PLR") to various pathological conditions has been reported by a number of prior art researchers. Alexandridis et al. (The Latent Period of The Pupil Light Reflex In Legions of The Optic Nerve, Ophthalmalogica, Basel, 182, 211–217, 1981) have shown a distinct prolongation in PLR latency (i.e., the time lag between stimulus and the onset of pupillary constriction) associated with optic nerve inflammation or atrophy. It was originally thought that this increase in the latency was due to the loss of sensory perception accompanying such abnormalities. Lowering the stimulus intensity incident on a normal eye increases the PLR latency while the PLR response amplitude and maximum speed of contraction decrease (see Lowenfeld et al., Influence of Pupil Size on Dynamics of Pupillary Movements, Amer. Jour. of Ophthal., 71, 347–362, 1971). People who suffer from abnormalities of the optic nerve generally have higher sensory thresholds, meaning that more light is required to obtain the same response (visual or pupillary) as a normal eye. Consequently, people with this condition generally have a diminished PLR similar to that obtained with a normal eye at a lower stimulus intensity. Thus, a loss of sensory perception can account for a slight increase in pupillary latency as well as the other characteristics of a diminished reflex. However, the findings of Lowenfeld et al. determined that the prolonged latency in cases of optic nerve inflammation or atrophy was beyond that to be expected from a loss of sensory perception alone. In fact, the Lowenfeld et al. study used the degree of prolongation in the latency to diagnose the type as well as the location of the neuropathy involved.

C. Ellis, in Journal of Neurology, Neurosurgery, and Psychiatry, 42, 1008–1017, 1979, presents a history of measurement and use of pupillary reaction, and a study of pupillary responses of patients with acute optic neuritis. In a study described by Ellis, an infrared television pupillometer was used. The pupillary diameter was measured from the television video frames using a pupillometer analyser system. The limit of resolution of timed events (presumably, the time between successive video frames) was 20 ms and the resolution of pupillary diameter was 0.03 mm. Subjects were dark adapted, and a 100 ms white light stimulus, focused to a 2.0 mm beam was delivered every eight seconds. Among other things, Ellis measured latency from stimulus to onset of pupillary constriction and maximum rate of pupillary constriction. It was found that patients with acute optic neuritis had prolonged latency in most cases. However, Ellis observed that the latency data was limited by the resolution of the equipment, and by the difficulties of defining exactly the onset of pupillary constriction.

Amblyopia, the "lazy eye syndrome" is another eye defect that increases the PLR latency. A study by Kase et al. (Pupillary Light Reflex in Amblyopia, Invest. Ophthal. and Vis. Sci, 467–471, 1981) using an infrared TV-camera based instrument with time resolution of 16 ms, showed that 10 of 15 patients with amblyopia had significant increases in latency (both direct and consensual) when the affected eye was stimulated. The remaining 5 has no measurable latency differences between the normal and affected eye. The fact that both eyes were affected equally upon stimulus of the damaged eye signifies that amblyopia is an afferent defect (retina to brain) and not an efferent impairment (brain to iris). The PLR amplitude and speed of constriction did not differ significantly from the values measured when the normal eye was stimulated. Also, there was no correlation between an increase in pupillary latency and a loss of visual acuity indicating separate sites and mechanisms for these two conditions. This might explain why most people do not notice the presence of amblyopia until detected clinically.

The presence of a normal PLR has been used subjectively for a long time in accessing the severity of intracranial damage. One study by Braakman et al. (Systematic Selection of Prognostic Features In Patients With Severe Head Injury, Neurosurgery, 6, 362–369, 1980) on the prognostic indicators of patients with severe head injuries showed the presence of a PLR to be highly-correlated with the survival rate of those patients. A similar study reported in the American Medical News Mar. 15, 1985, p.55) determined the PLR to be a good clinical assessment of possible recovery in coma patients. In this latter report, none of the 52 patients who showed no response to light ever recovered to "independent daily function." In contrast, 11 out of 27 patients who did show response to light regained independence in their daily lives.

A unilateral sluggish pupil has been reported as a sign of brain herniation, a stroke-causing condition (see AFP, Vol. 31, No. 3, page 192).

From the above, it is seen that prior investigators have recognized various possibilities in using pupillary response as a diagnostic tool. However, except for traditional relatively crude determinations (e.g. checking the pupils of a patient with a flashlight), sophisticated use of pupillary response parameters has not found widespread use in applications where it is believed to have tremendous potential; viz., in diagnosing the onset or presence of injury or disease, and in determining the presence of drugs or alcohol in the body. A primary reason for this lack of development is that prior art techniques and systems suffer from one or more of the following disadvantages:

(a) The cost of obtaining pupillary measurements, is high, since accurate equipment has tended to be relatively expensive to purchase and/or use.

(b) The resolution of the measurement of pupillary response is often not sufficient to permit determination of pupillary response parameters with accuracy that is needed for diagnosis.

(c) Artifacts in the measurement of pupillary response prevent obtainment of true pupillary response parameters that would provide a meaningful indicator of physical condition.

It is among the objects of the present invention to provide a method and apparatus for determination of pupillary response that overcomes problems of prior art techniques and systems.

SUMMARY OF THE INVENTION

Applicant has devised a method and apparatus for determination of pupillary response that can be implemented at reasonable cost and which operates at accuracies needed to obtain meaningful indications of a subject's physical condition. It has been observed that artifacts in pupillary response measurement data can have a substantial influence on the ultimately determined pupillary response parameters. As a result, unless they are dealt with, the artifacts can render the obtained response parameters useless or of little value. For example, a known artifact-causing phenomenon is the so-called "photomyoclonic reflex" ("PMR"), which involves motion of the eye in response to a visible light stimulus. Such motion of the eye occurs during important portions of the measurements of pupil size (which, over time, comprise the pupil response data). This causes the measurement instrument to "see" different geographical regions of the eye (having, for example, different relectivities) during the measurement process and thereby causes artifacts in the measurements which tend to mask the true pupillary response. In accordance with a feature hereof, pupillary response measurements are processed so as to achiever output response parameters that better represent the true pupillary response parameters, the effect of artifacts having been removed.

The present invention is not directed to diagnosis of a specific physical condition, as at the time of this application the method and apparatus hereof has not been clinically evaluated. However, applicant is convinced from prior studies by others, and from limited initial study of data obtained using the techniques and systems hereof under test conditions, that valuable diagnostic information can be obtained from accurate artifact-free pupillary response parameters.

In accordance with an embodiment of the invention, there is provided an apparatus for measuring the pupillary response of an eye, which includes means for establishing a dark field condition around the eye, and means, within the dark field, for irradiating at least a portion of the pupil and iris of the eye with infrared radiation. Means, also within the dark field, are provided for detecting the infrared radiation reflected from the eye, and for storing the quiescent level of detected radiation. Further means within the dark field are provided for irradiating the eye with a pulse of visible light. Means are provided for generating a difference signal representative of the difference between the detected infrared radiation and the stored quiescent level of infrared radiation. Means are also provided for recording the difference signal as a function of time, the recorded difference signal representing the pupillary response of the eye to a visible light pulse.

In a preferred embodiment of the invention, means are provided for processing the recorded signal to obtain a processed recorded signal in which artifacts due to eye movement have been removed. In this embodiment, the processing means includes means for fitting curves to different portions of the recorded signal, and means for obtaining the processed recorded signal from the fitted curves. The fitted curves include a first curve for the latency time between the pulse of visible light and the beginning of pupil constriction, a second curve for the time of acceleration of pupil constriction, and a third curve for the time of constant rate pupil constriction.

Pupillary latency time is believed to be a particularly important pupillary response parameter. In accordance with a form of the method of the invention, there is provided an improved technique for determining the latency of pupillary response of the eye, including the steps of: deriving a signal representative of measured pupil size as a function of time after a visible light stimulus; modifying the signal to remove therefrom artifacts due to eye movement; and determining the latency of pupillary response from the modified signal. In the preferred embodiment, the modifying of the signal includes fitting curves to different portions of the signal, correcting at least one of fitted curves, and deriving the modified signal from the curves, as corrected.

Further features and advantages of the invention will become more readily apparent from the following detailed description when taken in conjunction with the accompanying drawings.

BRIEF DESCRIPTION OF THE DRAWINGS

FIG. 3 is a diagram of the optical head of an embodiment of the invention, with FIG. 3A being a cross-section through the optical head, and FIG. 3B being a front view.

DESCRIPTION OF THE PREFERRED EMBODIMENT

Figure 1B:
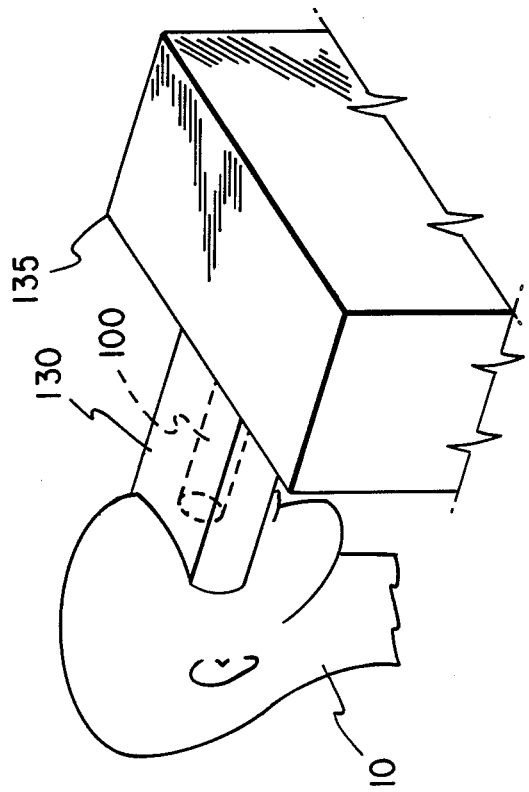
FIGS. 1A and 1B illustrate a patient and an example of the type of headgear that can be used in practicing the present invention.
Figure 1A:
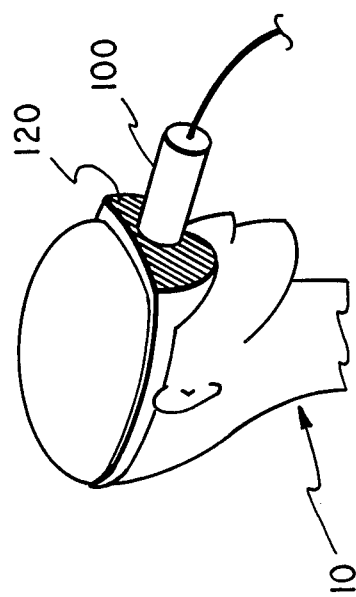
Figure 2:
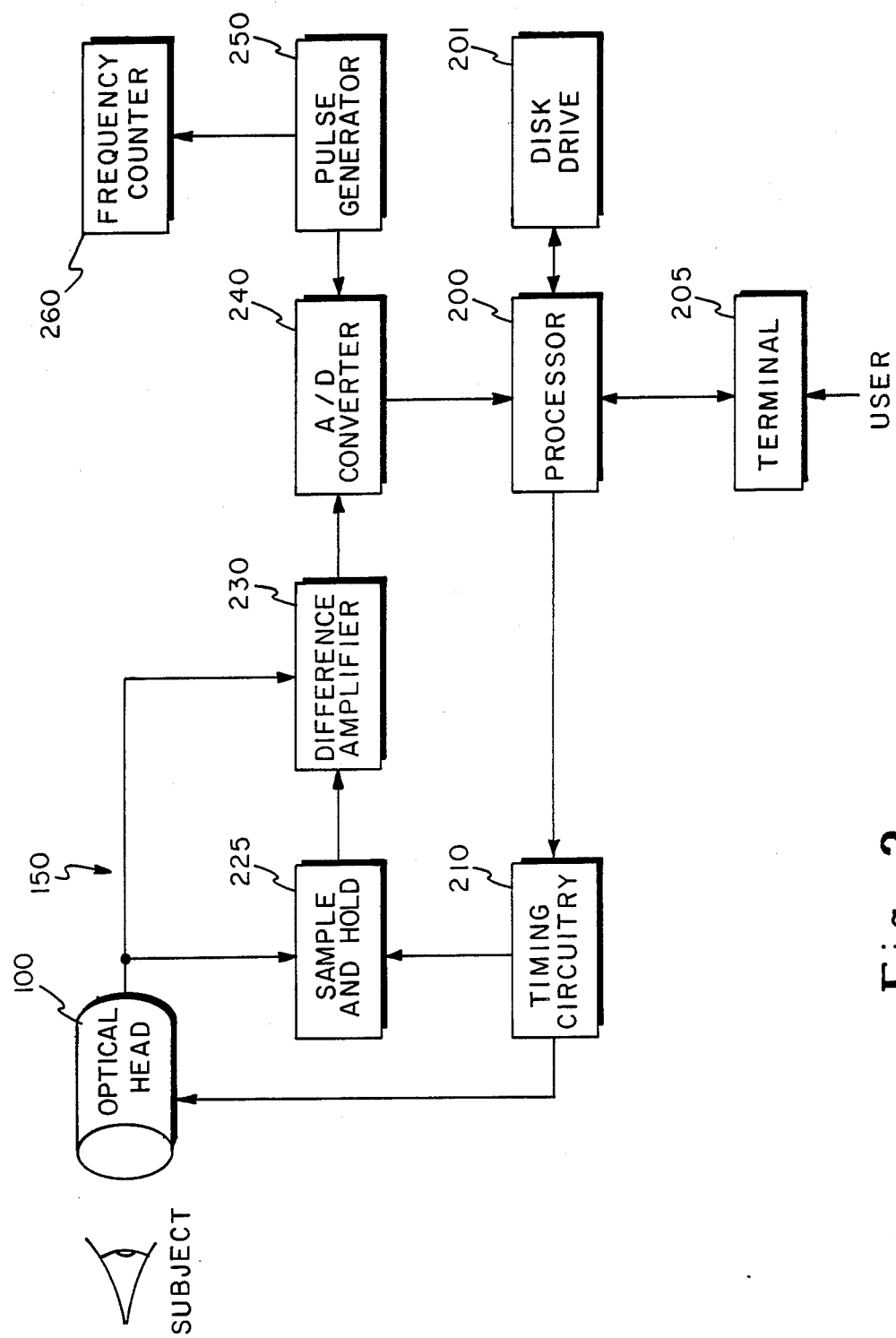
FIG. 2 is a block diagram of a system in accordance with an embodiment of the invention, and which can be used in practicing the method of the invention.

Referring to figs 1A and 1B there are shown sketches of a patient 10 being tested on equipment that includes an optical head 100 that is mounted in goggles 120 (in the FIG. 1A illustration) or in the headpiece 130 of a console 135 (in the FIG. 1B illustration)., In the FIG. 1A illustration, a cable is shown as being coupled to the optical head, and carries signals to and from the system 150 that is shown in FIG. 2. In the FIG. 1B illustration, the system 150, or portions thereof, can be in the console 135.

Preferably, both eyes should be dark-adapted. Also, means (not shown) can be employed for aligning the optical head with respect to the patient's eye. It will be understood that other suitable means can be employed for mounting the optical head with respect to the patient. Further, if testing is performed in the dark, the task of dark adaption will not require the enclosing headgear.

In embodiments hereof, measurements are obtained on a dark-adapted eye continuously illuminated with infrared radiation. The IR wavelength used (900 nm) does not stimulate the retina and therefore does not affect the pupillary light reflex. During the measurement, the eye is stimulated by a 20 ms pulse of green light generated by light emitting diodes. The IR reflectivity of the iris is much larger than that of the pupil. As a consequence, when the stimulated pupil constricts, the reflected IR radiation increases. This signal is imaged onto a detector which converts the reflected power into an electrical signal which is then sampled and processed.

FIG. 2 shows a block diagram of a system in accordance with an embodiment of the invention. A data scan can be initiated by typing a control character into a keyboard (not shown) associated with a terminal 205 and processor 200, for example a model PDP LSI/11, manufactured by Digital Equipment Corp. of Maynard, Mass. A logic pulse is then sent to a timing circuit 210. This pulse is delayed by 60 ms in the timing circuit 210 before switching on green visable light-emitting diodes in the optical head 100. The optical head 100 provides the visual stimulus to the dark-adapted eye as well as housing the IR light-emitting diodes, imaging system and IR detector/amplifier, to be described below.

During the 60 ms delay before the optical stimulus, a sample and hold amplifier 225 latches the dc (quiescent) level of IR reflection from the dilated pupil. Once constriction begins, the increasing pupillary light reflex signal from the detector/amplifier in optical head 100 is fed into a difference amplifier 230 which subtracts the latched dc voltage and amplifies the result, thereby increasing the dynamic range of the system. This signal is then coupled, via analog-to-digital converter 240, to processor 200. A pulse generator 250 clocks the A/D conversion at the desired sampling frequency which is accurately monitored by a frequency counter 260, for example a Model 6421 frequency counter made by Beckman Instrument Corp. In the present embodiment, each scan takes 4096 voltage samples that are initially stored on hard disk 201 associated with processor 200. A typical sampling frequency of 2.5 kHz yields approximately 1.6 sec (4096/2.5 kHz) of data, which is long enough to allow the peak constriction and the partial dilation in a normal pupillary light reflex to be recorded. At this sampling frequency the Nyquist criterion yields a time resolution of 0.8 ms. Other frequencies can be employed, however, if desired.

The optical head 100 of the FIG. 1 embodiment is illustrated in FIG. 3. The head includes a housing 101 in which are mounted four IR light emitting diodes 105 alternately spaced with four green LEDs 106. The IR LEDs 105 provide the sensing radiation and the green LEDs 106 provide the optical stimulus. In the center of the LED pattern is a lens 110 which images the reflected IR onto the active area 120A of a detector/amplifier 120, for example a Devar Model 529 detector. The detector is housed inside an aluminum sleeve 125 that fits inside the optical head. The detector and sleeve can be made removable from the optical head to facilitate the alignment of the subject's eye with respect to the imaging system. Once aligned, the detector can be inserted in the optical head and remain there for the duration of the data acquisition. In the illustrated embodiment, the housing is enclosed in a black Devlin outer casing. Leads from the LEDs, e.g. 105A, are coupled to the timing circuitry 210 (FIG. 2), and the detector cable 120A is coupled to the sample-and-hold circuit 225 and the difference amplifier 230.

Figure 4:
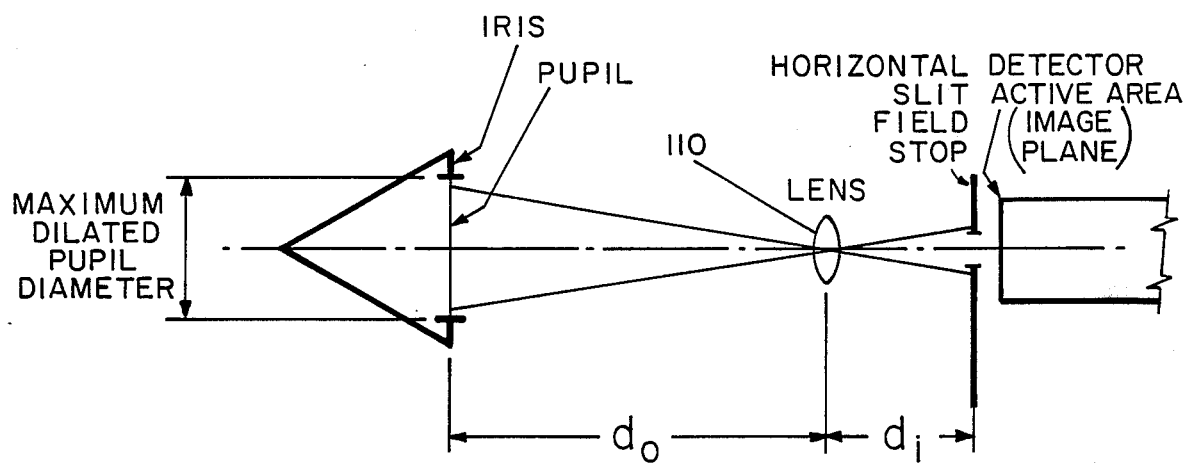
FIG. 4 is a simplified diagram of the optics which is useful in understanding the imaging of the infrared radiation reflected from the eye.
Figure 5:
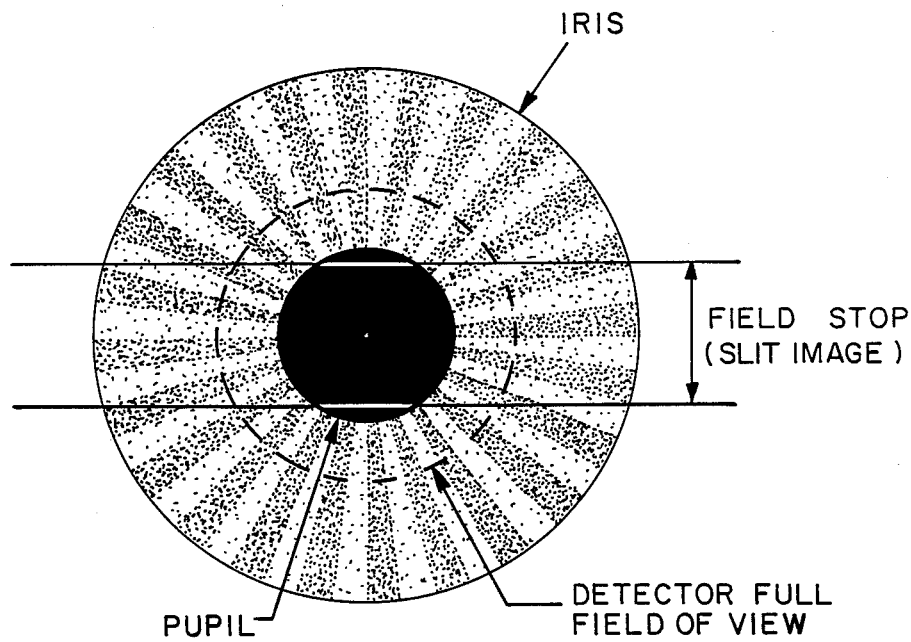
FIG. 5 is a diagram of the pupil and iris of the eye, and illustrates an example of a detector field of view, and the effect of imaging through a slit.

In the illustrated embodiment the imaging of the reflected IR signal from the eye onto the photodetector is accomplished using a single symmetrical convex lens 110, as shown further in FIG. 4. As the pupil constricts, the area of the iris in the field of view of the detector increases. Consequently, more IR radiation is reflected by the eye and imaged onto the detector (see also FIG. 5). In order to detect the initial constriction, the detector field of view is made larger than the maximum dilated pupil diameter of the subject. The maximum pupil diameter value is typically 6-7 mm (see Loewenfeld et al., Iris Mechanics, Influence of Pupil Size on Dynamics of Pupillary Movements, American Journal of Ophthalmology, 1971), depending on the person and the degree of dark adaptation. If the magnification of the imaging system is chosen so that the diameter of the dilated pupil matches the diameter of the detector active area, then $$M = d_i/d_o = D_d/D_d \tag{1}$$

where
M = magnification
$d_i$ = distance from lens to active area of detector
$d_o$ = distance from eye to lens
$D_d$ = diameter of detector active area
$D_p$ = diameter of pupil.

Combining Eq. (1) with the thin lens equation, gives $$d_i = f(1 + D_d/D_p) \tag{2}$$

$$d_o = f(1 + D_p/D_d) \tag{3}$$

where f is the focal length of the lens.

Figure 6:
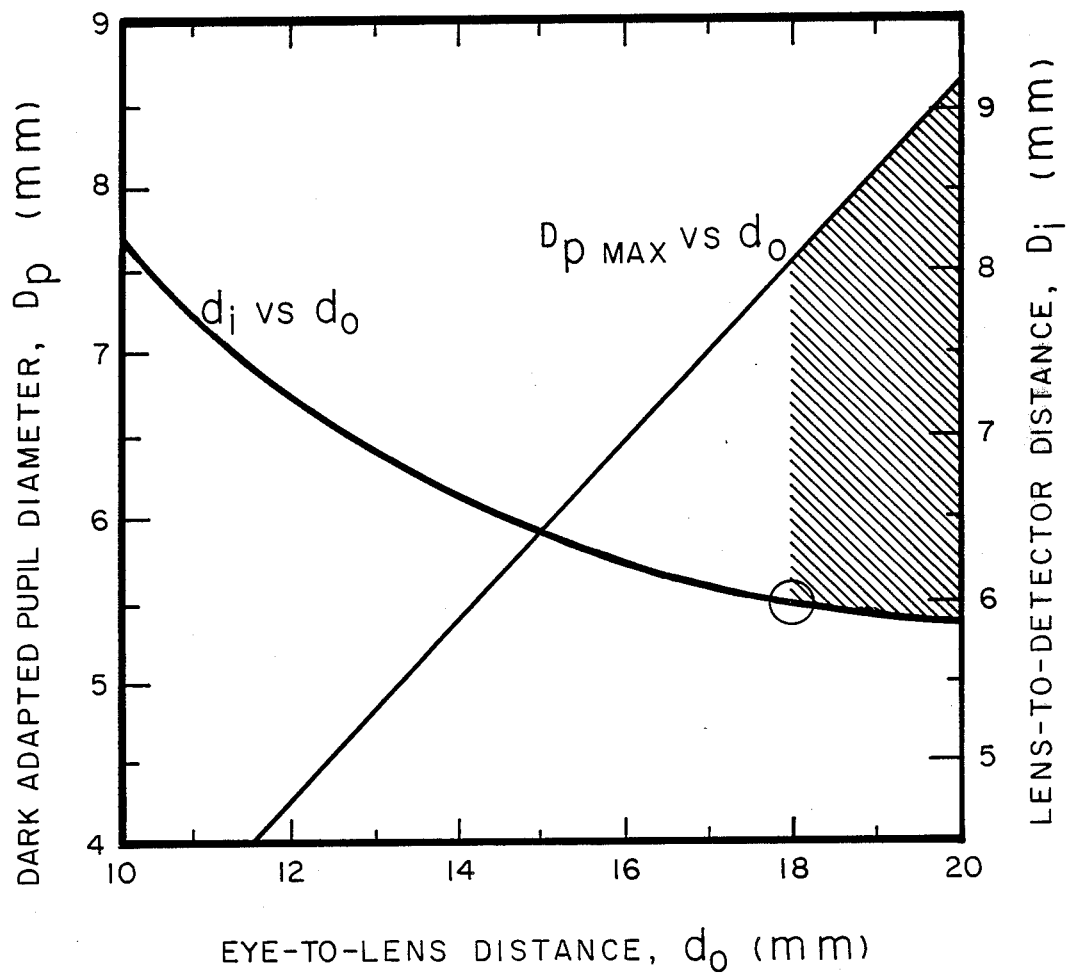
FIG. 6 is a graph that is useful in understanding relationships between the imaging parameters of the pupillary light response monitor in accordance with an embodiment of the invention.

FIG. 6 is a plot of $D_p$ versus $d_o$ for the fixed system parameters $D_d$=2.52 mm and f=4.5 mm. The straight line in the figure designates the maximum pupil diameter within the detector field of view for a given lens to detector distance $d_o$. For example, in order to entirely image a 7.5 mm pupil diameter the shaded region of the figure illustrates that $d_o$ must be greater than 18 mm. The right vertical axis of the figure represents the lens to detector distance $d_i$. The curved line signifies the image plane relating $d_i$ to $d_o$ for the lens used in the system. For proper imaging, the value of $d_i$ should fall as close to this curved line as possible. Assuming the $d_o$ of 18 mm used above, and finding the intersection with the curved line, $d_i$ is found to be approximately 6 mm. These values are denoted by the circle in FIG. 6.

Another consideration in the imaging system is the fact that the reflected power varies inversely with the square of $d_o$. Therefore to maintain strong signal levels, $d_o$ should be kept as small as possible. A field stop can be used on the front face of the detector to limit the vertical field of view. This is needed to reduce the effects of a reflex action of the eye to the stimulus. The reflex action of interest is known as the Photomyoclonic Reflex ("PMR"—see Johnson et al., The Photomyoclonic Reflex: An Artifact In The Clinical Electroretinogram, Bruit. Journal of Ophthal., 66, 1982).

In an embodiment hereof, the visual stimulus provided by the optical head is a 20 ms pulse of light from the green LED's. After the latency period, the resulting change in the pupil diameter ($\Delta D_p$), known as the response amplitude, depends on the visual energy in the stimulus reaching the retina. This energy is given by the product of the retinal intensity and the pulse width. As presented by Alpern et al. (The Dependence of The Photolpupil Response On Flash Duration Intensity, Jour, of Gen. Phys., 47, 265–278, 1963), $\Delta D_p$ for an individual will remain constant for pulse widths less than 150 ms provided the stimulus energy is constant. In other words, $\Delta D_p$ is constant provided the product (TxI) is constant where T is the pulse width ($\leq 150$ ms) and I is the stimulus intensity.

To calculate the retinal intensity one must consider not only the luminance of the source reaching the eye, but also the amount of light that reaches the retina. The unit of retinal intensity is the troland and is defined as "that intensity of stimulation that accompanies the use of a pupillary area of the square millimeter and an extended surface luminance of one candela per square meter," [Davson, The Physiology of The Eye, Little Brown & Co., G.B. 1963]. The LED source luminance can be expressed in units of retinal intensity by using the equation, $$I_r = \frac{7.85 \times 10^3 I_{LED} D_p}{d_s^2} \quad (4)$$

Where
  $I_r$ = retinal intensity (trolands)
  $I_{LED}$ = green LED luminous intensity (candela)
  $D_p$ = pupil diameter (mm)
  $d_s$ = distance from source to eye (cm).

For a typical LED output of 6 mcd, a source distance of 1.6 cm and a fully dilated pupil diameter of 8 mm, we obtain $I_r \simeq 150$ troland/LED.

Therefore, the energy illuminating the retina for the four green LEDs becomes $E_r \simeq 4 I_r T$ where
  T = pulse width (seconds)
  $E_r$ = retinal energy (troland-seconds).

With the 20 ms pulse width, $E_r$ for the pupil monitor is approximately 12 troland-seconds.

Figure 7:
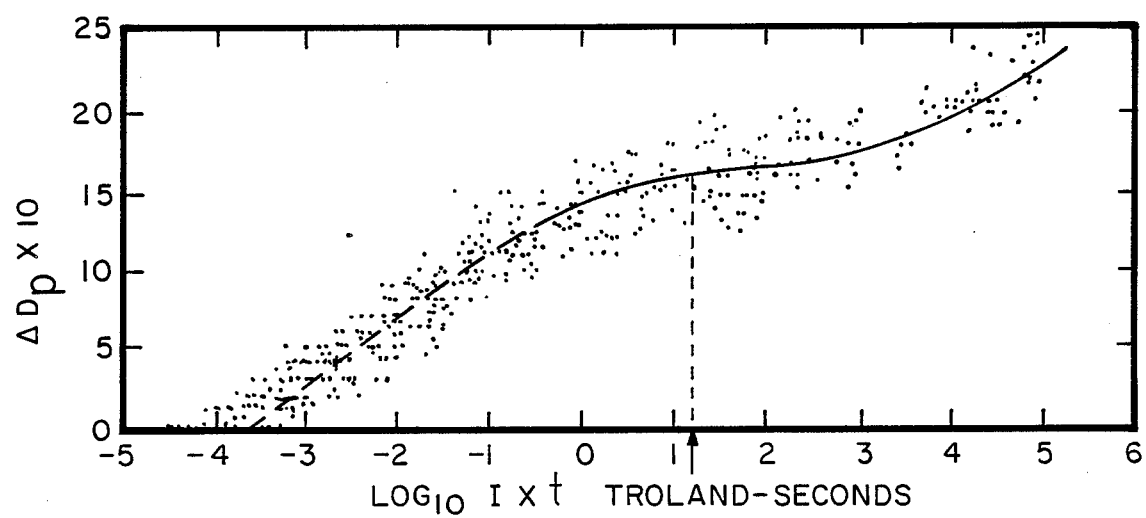
FIG. 7 is a graph illustrating the relationship between the amplitude of the pupil response and the energy of the light stimulus.

By comparing this value with the data plotted in FIG. 7 (Alpern et al., supra), the stimulus energy of the monitor corresponds to a response amplitude $\Delta D_p$ of approximately 1.5 mm. As shown in the Fig., the stimulus energy of 12 troland-seconds used in the pupil monitor falls on a rather flat portion of the response curve. [The smooth curve in the Fig. was drawn arbitrarily to show the trends.] This insures that small deviations in stimulus energy per individual should not significantly alter the response amplitude $\Delta D_p$. In fact, stimulus energies two orders of magnitude above or below this value would be required to significantly alter the amplitude of the response. Because there has been shown some correlation between $\Delta D_p$ and the pupillary latency (Ellis, The Pupillary Light Reflex in Normal Subjects, Brit. Jour. of Ophthal., 65, 754–759, 1981), the stimulus value of the monitor minimizes any bias of the latency measurement which may be caused by slight variations in the stimulus intensity.

When illuminating the eye with radiation (especially outside of the visible spectrum), care must be taken to insure that the radiation levels are safe. The limiting parameter to consider in this case is the power density of the imaged radiation on the retina. The Maximum Permissible Exposure (MPE) for the IR wavelength used in the monitor (900 nm), as given in Sliney et al. (Evaluation of Optical Radiation Hazards, Appl. Opt., 12, 1–24, 1973), is 100 mw/cm². The preferred embodiment employs IR radiation levels much less than this rating.

Figure 8:
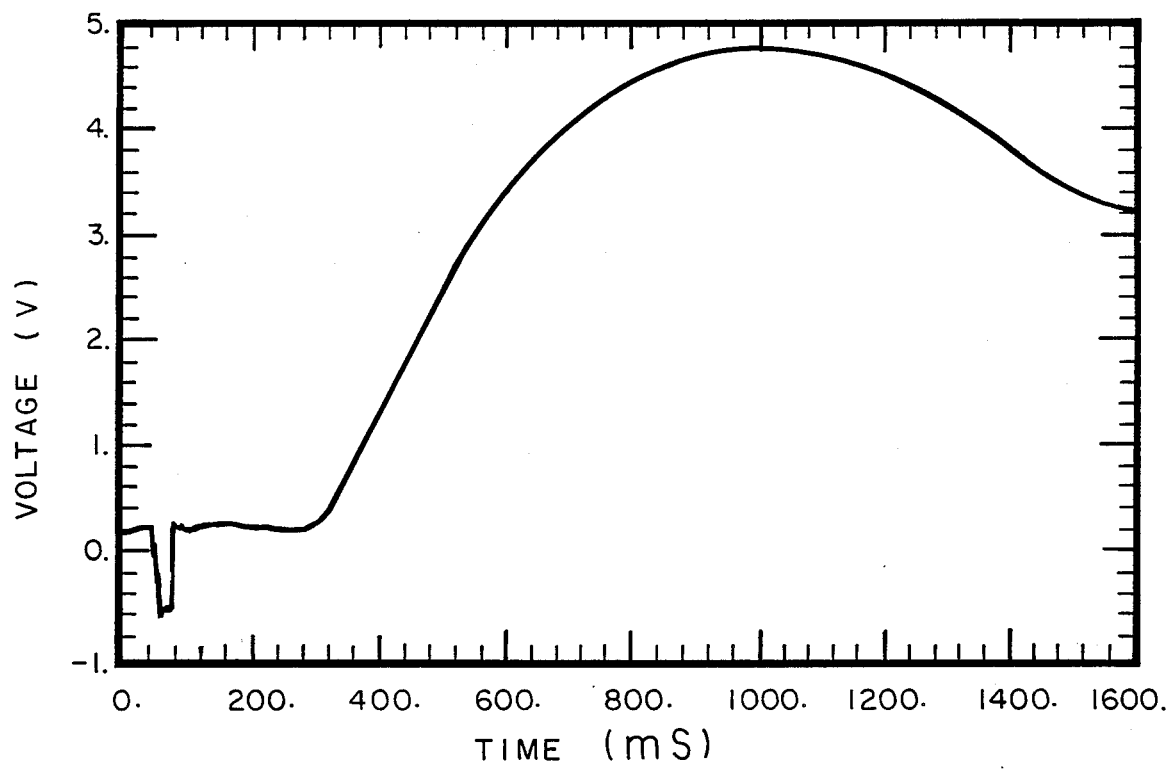
FIG. 8 is a graph which illustrates a typical pupillary light response signal.

A typical pupillary light response (PLR) signal is plotted in FIG. 8. The negative amplitude pulse at approximately 60 ms is due to the visual stimulus. When the green LEDs are pulsed, the higher current load reduces the dc power supply voltage and causes the output of the IR LEDs to decrease slightly. Because the detector in the monitor is most sensitive to IR radiation, the detector voltage also decreases. This negative pulse in the PLR signal serves as an accurate marker for the initiation time of the stimulus. Approximately 200 ms after the stimulus, the pupil begins to constrict. This time period is known as the pupillary latency. Once constriction begins, the area of the iris with respect to that of the pupil in the detector's field of view increases. The IR reflectivity of the iris is greater than that of the pupil and the PLR monitor detects this differential reflection. Thus, upon constriction, the intensity of the reflected IR signal increases. Anywhere from about 500–800 ms after the stimulus, the pupil reaches maximum constriction. Since the visual stimulus is a pulse of light, the pupil eventually begins to dilate. The signal level decreases as the pupil dilates and the iris area in the detector's field of view decreases.

In the present embodiment, the PLR monitor does not measure the absolute pupil diameter. Although the signal level is proportional to the iris area (and the complement of the pupil area), variations in iris color as well as in optical alignment can also affect this level. In the present embodiment, the monitor signal is actually a measure of the relative pupil area. Measurement of the changes in the relative pupil area can be used to determine important PLR parameters such as latency, sphincter acceleration time, speed of constriction, and maximum constriction time. To obtain these parameters accurately, it is first necessary to develop an approximate model for the PLR signal.

Due to the greater IR reflectivity of the iris with respect to that of the pupil, the detector output voltage can be modeled as $$V_d(t) = V_s + \eta A_i(t) \quad (5)$$

where
  $A_i(t)$ = area of the iris imaged onto the detector (mm₂)
  $V_s$ = equivalent output voltage for an iris area of zero (v)
  $\eta$ = equivalent system responsivity (V/mm²).

It is more convenient to express the iris area and detector voltage in terms of the pupil area $A_p(t)$, $$A_i(t) = A_o - A_p(t) \qquad (6)$$

$$V_d(t) = V_{s+\eta[A_o - A_p(t)]} = V_o - \eta A_p(t), \qquad (7)$$

where
 $A_o$ = total area imaged onto the detector (mm²)
 $V_o = V_{s+\eta A_o}$ = equivalent output voltage for a pupil area of zero (V).

The system responsivity depends on many factors including IR illumination levels, iris color, system alignment and detector sensitivity. It is more convenient to work with the normalized detector voltage which is defined as $$S(t) = \frac{V_d(t) - (V_d)_{min}}{(V_d)_{max} - (V_d)_{min}} = \frac{A_{max} - A_p(t)}{A_{max} - A_{min}} \qquad (8)$$

where
 $A_{max}$ = maximum pupil area (mm²)
 $A_{min}$ = minimum pupil area (mm²)
 $(V_d)_{min}$ = voltage level at onset of constriction (V)
 $(V_d)_{max}$ = voltage level at maximum pupil constriction (V).

Thus, S(t) is equal to one at maximum pupil constriction where $A_p = A_{min}$ and is equal to zero at maximum pupil dilation where $A_p = A_{max}$. Once the latency time and the maximum constriction time of the PLR signal have been determined, the corresponding voltages $(V_d)_{min}$ and $(V_d)_{max}$ are used to convert the PLR signal to percentages, with 100% indicating full constriction. In referencing the normalized plots, the terminology PMC (percentage of maximum constriction) is used.

Figure 9:
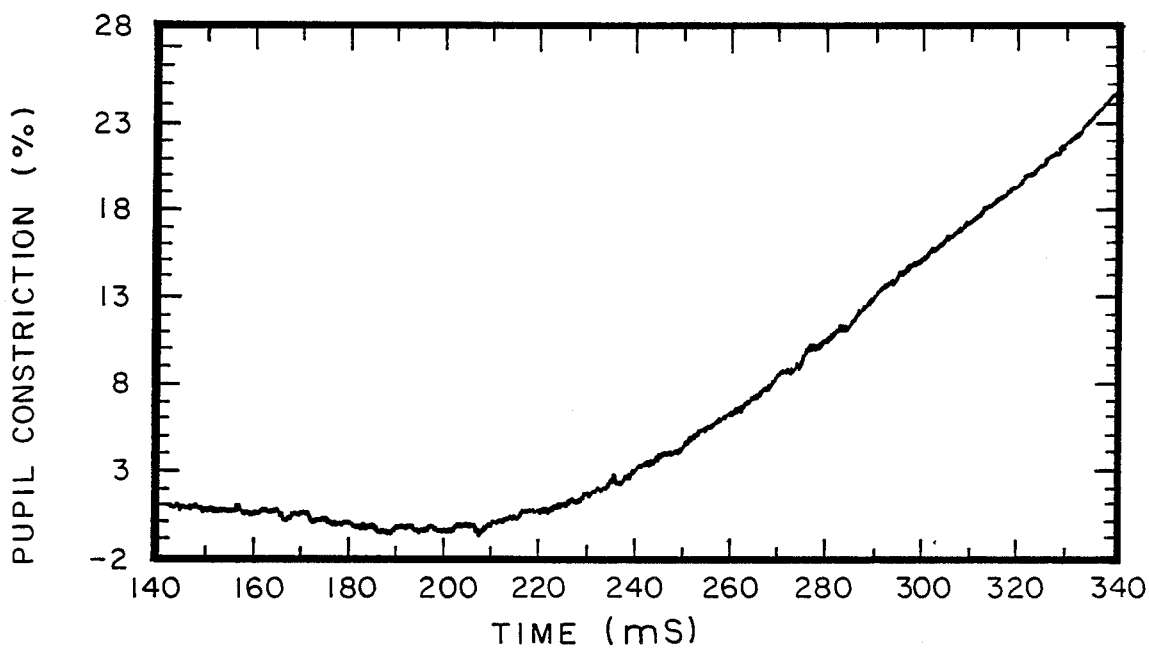
FIG. 9 is a graph illustrating a normalized pupillary light response signal, showing the region of the signal just before, during, and just after the onset of pupil constriction.

The manner of estimating latency will be treated next. FIG. 9 is an expanded plot of the normalized PLR signal near the onset of constriction. The small scale fluctuations in the signal are caused by detector noise, RF interference from the computer and quantization noise in the A/D converter. The 12 bit A/D converter has a voltage range of ±10 V which corresponds to a quantizing level of 4.88 mV. Thus, the fundamental noise level of the PLR monitor of the present embodiment is 4.88 mV.

Ideally, the signal level should be constant and near zero prior to constriction. However, the presence of eye movement and/or blinking due to the Photomyoclonic Reflex (PMR) can introduce artifacts into the signal. For example, the slight downward slope of the signal in FIG. 9 prior to the onset of constriction is due to the PMR. Signal artifacts such as this should be taken into account to obtain accurate estimates of the PLR parameters.

Figure 10:
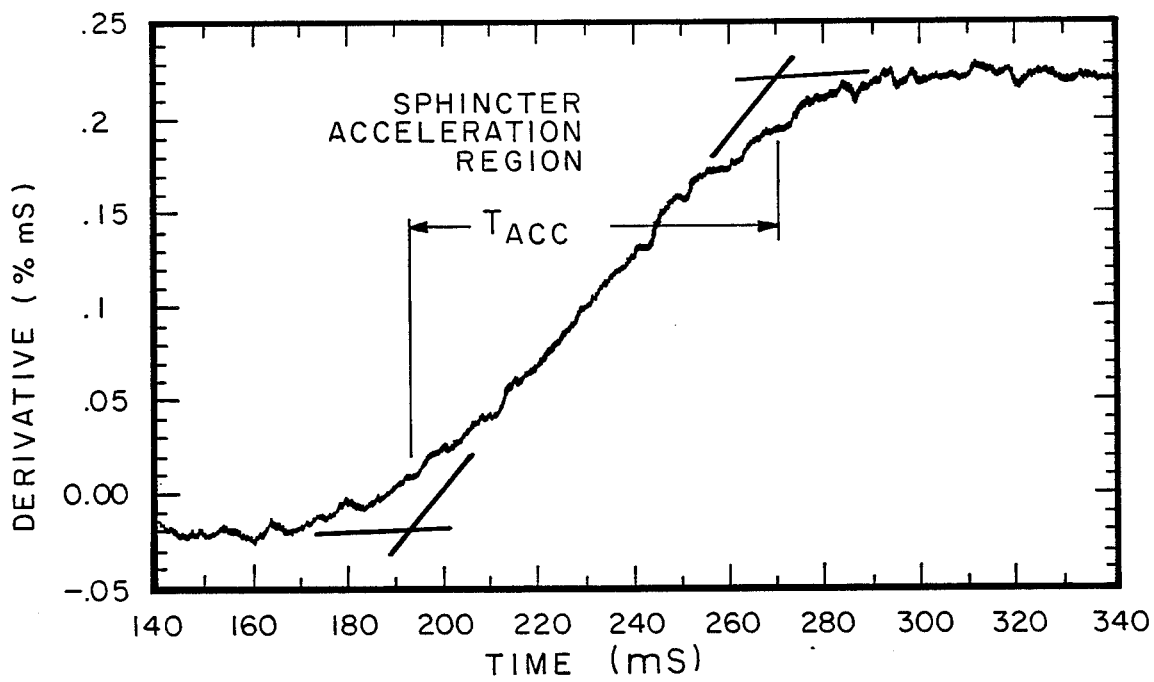
FIG. 10 illustrates, as a function of time, the temporal derivative of the normalized pupillary light response signal during the same time frame as in FIG. 9.

As the pupil begins to constrict the PLR signal increases approximately quadratically. FIG. 10 is a plot of the temporal derivative applied to this region of the response curve. The derivative is constant and near zero prior to constriction, is linear during the acceleration phase and then is constant afterwards. Thus, if $T_{LAT}$ denotes the time at which constriction begins (measured from the stimulus) and $T_{ACC}$ denotes the duration of the acceleration phase, the PLR signal can be modeled as $$S(t) = \begin{cases} \beta_1 t; & 0 \leq t \leq T_{LAT} \\ v_A(t - T_{LAT})^2 + \beta_2(t - T_{LAT}) + c; \\ \quad T_{LAT} \leq t \leq T_{LAT} + T_{ACC} \\ \beta_3(t - T_{LAT} - T_{ACC}); & T_{LAT} + T_{ACC} \leq t \end{cases} \qquad (9)$$

The latency and acceleration times can be determined by fitting Eq. (9) to the measured data and then solving for $T_{LAT}$ and $T_{ACC}$. The linear terms $\beta_1$ and $\beta_2$ are introduced to account for signal artifacts due to PMR. If these terms are zero, the PLR signal in the quadratic region is $$S(t) = v_A(t - T_{LAT})^2 + c. \qquad (10)$$

The minimum of this parabola occurs at the time $T_{LAT}$. In general, $\beta_1$ and $\beta_2$ will not be zero so that the minimum of the parabola occurs at the time $$T_{MIN} = T_{LAT} - \frac{\beta_2}{2v_A}. \qquad (11)$$

Equation (11) forms the basis of the latency estimate. Solving for $T_{LAT}$ yields the estimate in terms of $T_{MIN}$, $\beta_2$ and $v_A$. By applying a least-square quadratic fit to the data in the region $T_{LAT} \leq t \leq T_{LAT} + T_{ACC}$, the parameters $T_{MIN}$ and $v_A$ can be directly estimated using the regression coefficients. To see this, the signal model given in Eq. (9) for this region is expanded, as follows:

$$S(t) = v_A t^2 + (\beta_2 - 2v_A T_{LAT})t + v_A T_{LAT}^2 - \beta_2 T_{LAT} + c. \qquad (12)$$

The regression analysis of the measured data yields $$S_{fit}(t) = \hat{v}_A t^2 + \hat{m} t + \hat{c}' \qquad (13)$$

where $\hat{m} = \hat{\beta}_2 - 2\hat{v}_A T_{LAT} \qquad (14)$ $\hat{c}' = \hat{v}_A T_{LAT}^2 - \hat{\beta}_2 T_{LAT} + \hat{c}.$ The hat denotes that the parameters are least-square estimates. A direct estimate of $v_A$ can be obtained from the quadratic fit coefficient as shown in Eq. (13). Also an estimate to $T_{MIN}$ can easily be determined from the curve fit estimates by $$T_{MIN} = \frac{-\hat{m}}{2\hat{v}_A}. \qquad (15)$$

Note, however, from Eqs. (12) and (13) that the linear regression coefficient m does not directly estimate the parameter $\beta_2$. Therefore, to obtain the latency, the parameter $\beta_2$ must be estimated. Based on the premises that the true PLR signal is parabolic during the acceleration phase and that this phase is short in duration, $\beta_2$ may be assumed to be approximately equal to $\beta_1$. That is, it is assumed that the linear component present in the quadratic region is identical to the linear component introduced by artifacts in the signal prior to constriction. The slop $\beta_1$ is determined by fitting a straight line to the signal in the region prior to the onset of constriction. As estimate of the latency can be obtained from the calculated values of $\hat{T}_{MIN}$, $\hat{v}_A$, and $\beta_1$ by using Eq. (11), $$\hat{T}_{LAT} = \hat{T}_{MIN} + \frac{\hat{\beta}_1}{2\hat{v}_A} = T_{LAT} - \frac{(\hat{\beta}_2 - \hat{\beta}_1)}{2\hat{v}_A} \simeq T_{LAT} \quad (16)$$

where
- $\hat{T}_{LAT}$ = estimated latency (ms)
- $\hat{T}_{MIN}$ = estimated time of the minimum of the least-square quadratic fit to the signal in the acceleration region ($T_{LAT} < t < T_{LAT} + T_{ACC}$) (ms)
- $\hat{v}_A$ = quadratic coefficient of the least-square quadratic fit to the signal in the acceleration region ($T_{LAT} < t < T_{LAT} + T_{ACC}$) (%/ms$^2$)
- $\beta_1$ = slope of least-square linear fit to the signal in the region prior to the onset of pupil constriction ($t < T_{LAT}$) (%/ms).

Thus, if the signal is accurately modeled by Eq. (9), and if the artifact signal does not change significantly during the acceleration phase so that $\beta_2 \simeq \beta_1$, the estimated latency given by Eq. (16) will be approximately equal to the true latency time.

Figure 11:
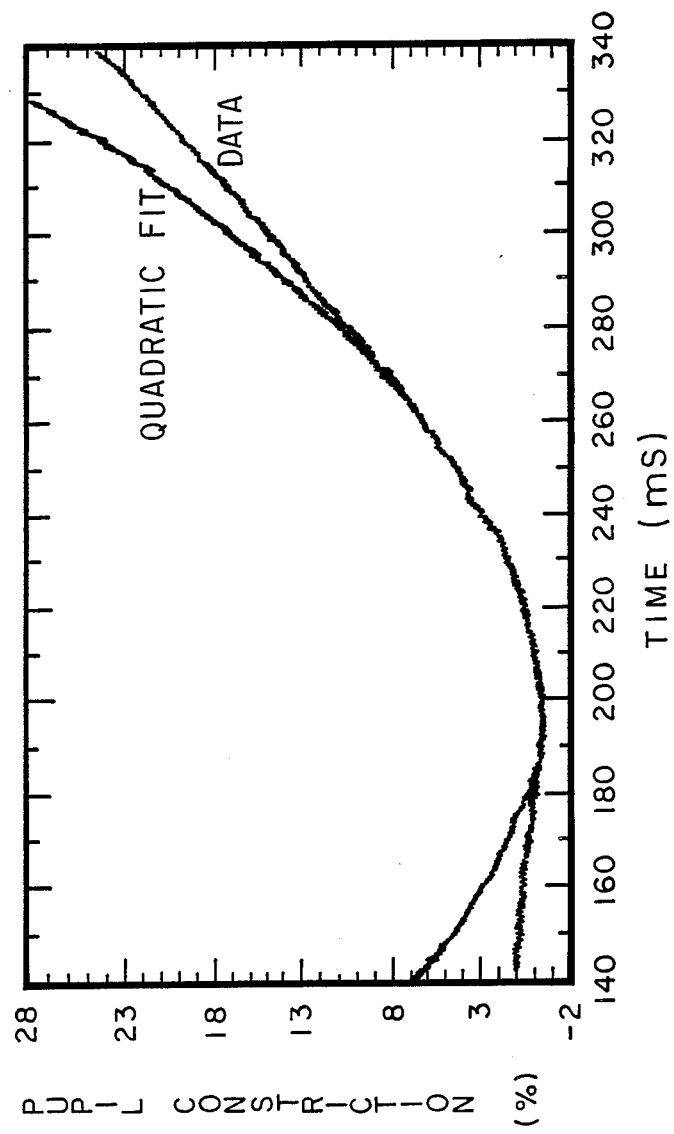
FIG. 11 shows the result of a least-square quadratic fit to the normalized pupillary light response signal in the region of the onset of pupil constriction.

FIG. 11 shows the resulting quadratic fit to the PLR data curve of FIG. 9. Notice the agreement in the fit until the 5-10 PMC points. From here the curve becomes quite linear, until the 70-80 PMC points where the rate of constriction begins to decrease as the pupil approaches maximum constriction.

Another PLR parameter of interest is the duration of the quadratic region. Referring to FIG. 11, one can see that the data are quadratic for only a short time period. This time period corresponds to the acceleration of the iris by the sphincter muscle and its duration is called the sphincter acceleration time. The acceleration time is primarily a measure of muscle tone as opposed to the speed of the neurological pathway.

The sphincter acceleration time ($T_{ACC}$) can be estimated by noting that the transition of the signal curve from the acceleration region to the linear region is continuous and smooth. The acceleration phase ends when the slope of the quadratic curve equals the slope of the linear curve (see FIGS. 10 and 11). By equating the temporal derivative of the model curves in Eq. (9) at $t = T_{LAT} + T_{ACC}$, we have $$2v_A T_{ACC} + \beta_2 = \beta_3, \quad (17)$$

which gives $$T_{ACC} = \frac{\beta_3 - \beta_2}{2v_A}. \quad (18)$$

Assuming again that $\beta_2 \simeq \beta_1$, then the estimated acceleration time becomes $$\hat{T}_{ACC} \simeq \frac{\hat{\beta}_3 - \hat{\beta}_1}{2\hat{v}_A} \simeq T_{ACC} \quad (19)$$

where $\beta_3$ = slope of linear least-square fit to the signal just after the acceleration region ($T_{LAT} + T_{ACC} \leq t$) (%/ms).

Also of interest in the PLR signal is the velocity or speed of constriction ($S_{CON}$). Typically the PLR curve is linear for most of the constriction phase of the light reflex (5-10 to 70-80 PMC). For this analysis, the speed of constriction was obtained from a linear regression fit on 20 ms of data centered at the 15 PMC point. This parameter is simply $\beta_3$ as defined in the model curve Eq. (9), $$\hat{S}_{CON} = \hat{\beta}_3 \ (\%/ms) \quad (20)$$

Figure 12:
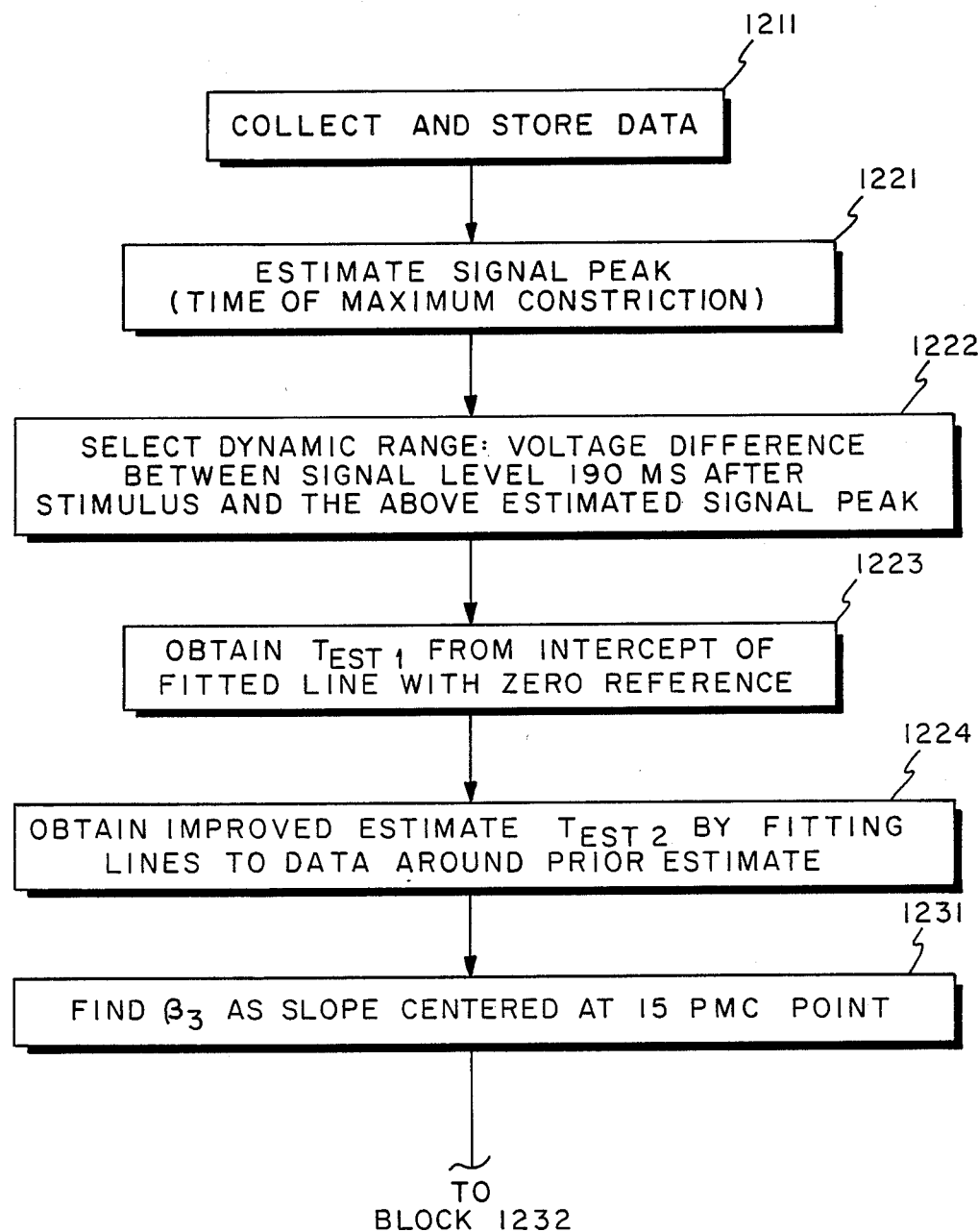
FIG. 12 which includes FIGS. 12A, 12B and 12C placed one-below-another, is a flow diagram of a routine for programming a processor to implement a technique for obtaining a corrected recorded pupillary response signal and/or pupillary response parameters, in accordance with an embodiment of the invention.
Figure 12B:
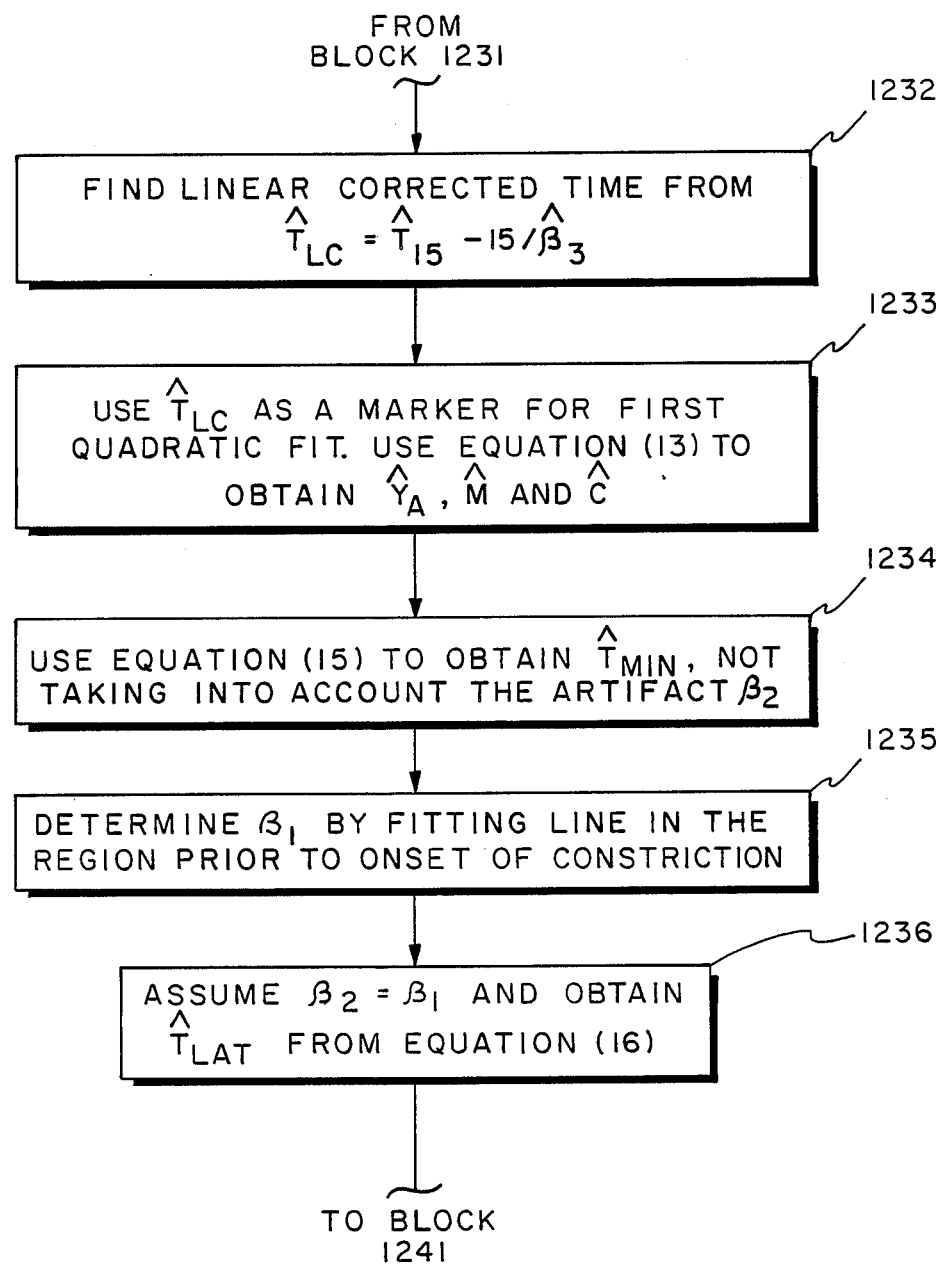
Figure 12C:
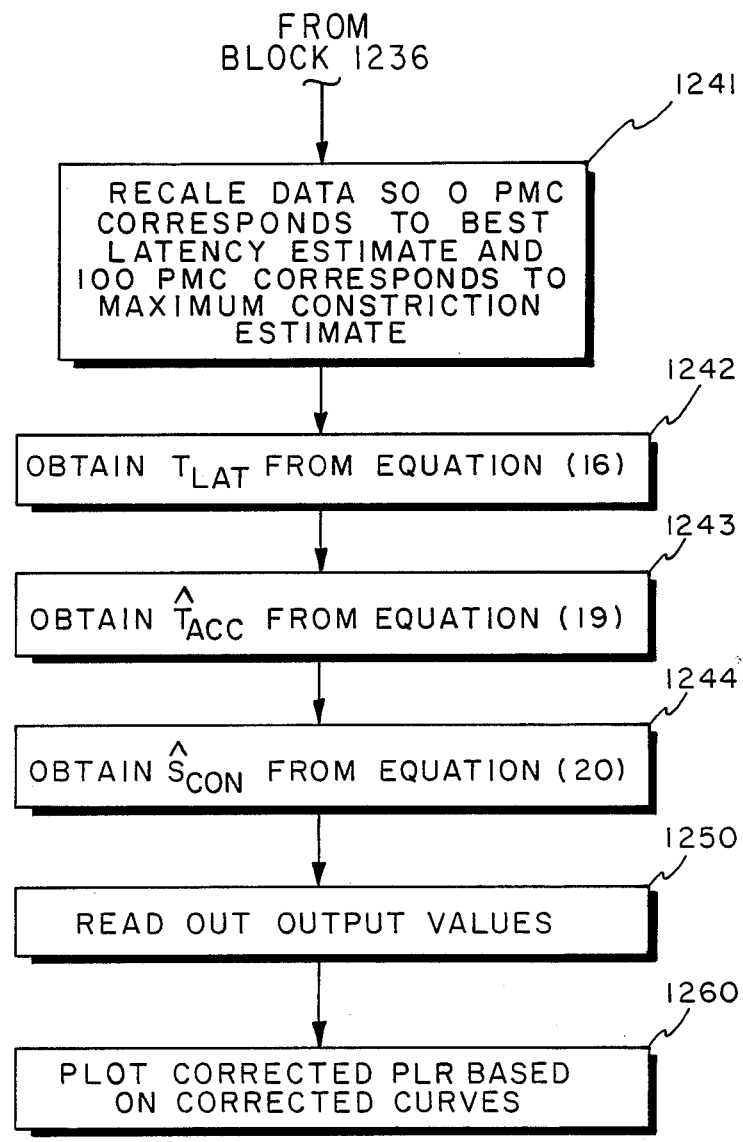

Any suitable general purpose or special purpose computer can be used to implement the method of obtaining pupillary response parameters consistent with the procedure as set forth. The processor 200 (FIG. 2), or a different processor, for example an IBM Personal Computer, can be employed. FIG. 12 is a flow diagram of a routing that can be used to control the processor to implement the described technique. The block 1211 represents the collection and storage of the raw data, as previously described, using the equipment of FIG. 2 on a particular subject, as previously discussed. Processing of the raw data can then be initiated. The block 1221 is entered, this block representing initial computation of the time of maximum constriction of the pupil. Any suitable technique of determining the maximum of a series of data points can be employed. For example, the centroid of points around a zero slope can be was used to obtain this estimate. The blocks 1222 and 1223 represent the obtainment of a crude estimate of $T_{LAT}$ by first assuming that the dynamic range is between the level at about the onset of constriction (assumed initially, for this purpose, to be at 190 ms) and the estimated signal peak (block 1222). The block 1223 then represents the obtainment of the estimate, designated $T_{est1}$, by fitting a line between the 10% and 30% points of the dynamic range, with $T_{est1}$ being taken from the intercept of this fitted line with the assumed zero difference line. The block 1224 is then entered, this block representing the improvement of the estimate by taking data 30 ms to the left and 40 ms to the right of $T_{est1}$, fitting a line through each, and taking the intersection as the next estimate, designated $T_{est2}$.

The block 1231 is then entered, this block representing the step of taking the time corresponding to 15% of maximum constriction ("PMC"), and determining the slope centered at this 15 PMC point. This slope is designated as $\ominus_3$. Next, a time called the "linear corrected time", $\hat{T}_{LC}$ is determined (block 1232) using the equation $\hat{T}_{LC} = \hat{T}_{15} - 15/\ominus_3$. This time, $\hat{T}_{LC}$, is the latency time assuming the data were entirely linear at the onset of constriction, with a slope equal to $\beta_3$. The block 1233 is then entered, this block representing using $\hat{T}_{LC}$ as a marker to center the first quadratic fit. This ensures that the quadratic fit is within the quadratic region just after the onset of constriction. As previously described, equation (13) is used, employing a least-square quadratic fit, to obtain the values $\hat{v}_A$, $\hat{m}$ and $\hat{c}$. Equation (15) can then be utilized (block 1234) to get $\hat{T}_{min}$, which is minimum of the quadratic before taking into account the artifact that causes $\beta_2$. Next, $\beta_1$ is determined (block 1235) by fitting a straight line in the region prior to the onset of constriction (for the 15 ms prior to the latest estimate of the onset of constriction, in this embodiment). Then, as represented by block 1236, it is assumed that $\beta_2 = \beta_1$ (as previously described, and $T_{LAT}$ is obtained using equation (16).

Further processing can then be implemented, if desired, beginning with block 1241, which represents the rescaling of data so that 0 PMC corresponds to the amplitude at the previously determined latency time, $T_{LAT}$. Final parameter estimates can then be obtained for latency time $T_{LAT}$ using equation (16) (block 1242), time of latency acceleration $\hat{T}_{ACC}$ using equation (19) (block 1234), and speed of constriction $\hat{S}_{CON}$ using equation (20) (block 1244). (If desired, further iterations can be performed.) These and other determined pupillary response parameters (e.g. time to maximum constriction), can then be read out and/or recorded (block 1250). Also, a corrected pupillary response signal can be output, based on the curves of equation (9) (block 1260).

We claim:

1. Apparatus for measuring the pupillary response of an eye, comprising:
    means for establishing a dark field condition around the eye;
    means, within said dark field, for irradiating at least a portion of the pupil and iris of the eye with infrared radiation;
    means, within said dark field, for detecting infrared radiation reflected from the eye;
    means for storing the quiescent level of detected infrared radiation;
    means, within said dark field, for irradiating the eye with a pulse of visible light;
    means for generating a difference signal representative of the difference between the detected infrared radiation and the stored quiescent level of infrared radiation; and
    means for recording said difference signal as a function of time, the recorded signal representing the pupillary response of the eye to a visible light pulse.

2. Apparatus as defined by claim 1, wherein said detecting means includes a slit for restricting the vertical extent of infrared radiation that is detected.

3. Apparatus as defined by claim 1, wherein said means for irradiating with infrared radiation and said means for irradiating with visible light together comprise a circular array of light-emitting devices, the array having alternating infrared and visible light emitters.

4. Apparatus as defined by claim 3, wherein said detecting means includes a detector in the center of said circular array of emitters.

5. Apparatus as defined by claim 1, further comprising means for processing the recorded signal to obtain a processed recorded signal in which artifacts due to eye movement have been removed.

6. Apparatus as defined by claim 5, wherein said processing means comprises means for fitting curves to different portions of the recorded signal, and means for obtaining the processed recorded signal from the fitted curves.

7. Apparatus as defined by claim 1, further comprising means for processing the recorded signal by fitting curves to different portions of the recorded signal, means for obtaining a processed recorded signal from the fitted curves, and means for determining at least one pupillary response parameter from the processed recorded signal.

8. Apparatus as defined by claim 6, wherein said fitted curves include a first curve for the latency time between the pulse of visible light and the beginning of pupil constriction, a second curve for the time of acceleration of pupil constriction, and a third curve for the time of constant pupil constriction.

9. Apparatus as defined by claim 7, wherein said fitted curves include a first curve for the latency time between the pulse of visible light and the beginning of pupil constriction, a second curve for the time of acceleration of pupil constriction, and a third curve for the time of constant pupil constriction.

10. Apparatus as defined by claim 8, wherein said first and third curves are linear and said second curve is parabolic.

11. Apparatus as defined by claim 9, wherein said first and third curves are linear and said second curve is parabolic.

12. Apparatus as defined by claim 10, wherein said second curve is corrected as a function of the slope of said first curve.

13. Apparatus as defined by claim 11, wherein said second curve is corrected as a function of the slope of said first curve.

14. Apparatus as defined by claim 7, wherein said at least one pupillary response parameter is latency time.

15. Apparatus as defined by claim 7, wherein said at least one pupillary response parameter is the rate of acceleration of pupil constriction.

16. Apparatus as defined by claim 7, wherein said at least one pupillary response parameter is the constant velocity of pupil constriction.

17. Apparatus as defined by claim 12, further comprising means for determining latency of pupillary response from the processed recorded signal.

18. A method for measuring the pupillary response of an eye, comprising the steps of:
    establishing a dark field condition around the eye;
    irradiating at least a portion of the pupil and iris of the eye with infrared radiation;
    detecting infrared radiation reflected from the eye;
    irradiating the eye with a pulse of visible light;
    recording, as a function of time, a signal which depends upon the detected level of reflected infrared radiation, the recorded signal representing the pupillary response of the eye to a visible light pulse; and
    processing the recorded signal to obtain a processed recorded signal in which artifacts due to eye movement have been removed, said processing step comprising fitting curves to different portions of the recorded signal, and obtaining the processed recorded signal from the fitted curves.

19. The method as defined by claim 18, further comprising the step of determining at least one pupillary response parameter from the processed recorded signal.

20. The method as defined in claim 19, wherein said fitted curves include a first curve for the latency time between the pulse of visible light and the beginning of pupil constriction, a second curve for the time of acceleration of pupil constriction, and a third curve for the time of constant pupil constriction.

21. The method as defined by claim 20, wherein said first and third curves are linear and said second curve is parabolic.

22. The method as defined by claim 21, wherein said second curve is corrected as a function of the slope of said first curve.

23. The method as defined by claim 19, wherein said at least one pupillary response parameter is latency time.

24. The method as defined by claim 19, wherein said at least one pupillary response parameter is the rate of acceleration of pupil constriction.

25. The method as defined by claim 19, wherein said at least one pupillary response parameter is the constant velocity of pupil constriction.

26. A method for determining the latency of pupillary response of the eye, comprising the steps of:
    deriving a signal representative of measured pupil size as a function of time after a visible light stimulus;

modifying the signal to remove therefrom artifacts due to eye movement, said modifying of the signal including the steps of fitting curves to different portions of the signal, and obtaining the modified signal from the fitted curves; and determining the latency of pupillary response from the modified signal.

27. The method as defined by claim 26, wherein said modifying of the signal includes correcting at least one of the fitted curves, and deriving the modified signal from the curves, as corrected.

28. The method as defined by claim 27, wherein the fitted curves include a first curve for the latency time between the pulse of visible light and the beginning of pupil constriction, a second curve for the time of acceleration of pupil constriction, and a third curve for the time of constant pupil constriction.

29. The method as defined by claim 28, wherein said first and third curves are linear and said second curve is parabolic.

30. The method as defined by claim 29, wherein said second curve is corrected as a function of the slope of the first curve.

31. A method for obtaining an improved recording of pupillary response of the eye, comprising the steps of:

deriving a signal representative of measured pupil size as a function of time after a visible light stimulus;

modifying the signal to remove therefrom artifacts due to eye movement, said modifying of the signal including fitting curves to different portions of the signal, correcting at least one of the fitted curves, and deriving the modified signal from the curves, as corrected; and producing a recording of the modified signal.

32. The method as defined by claim 31, wherein the fitted curves include a first curve for the latency time between the pulse of visible light and the beginning of pupil constriction, a second curve for the time of acceleration of pupil constriction, and a third curve for the time of constant pupil constriction.

33. The method as defined by claim 32, wherein said first and third curves are linear and said second curve is parabolic.

34. The method as defined by claim 33, wherein said second curve is corrected as a function of the slope of the first curve.

* * * * *